United States Patent
Allen et al.

(10) Patent No.: US 9,452,025 B2
(45) Date of Patent: Sep. 27, 2016

(54) MEDICAL INSTRUMENT HOLDER AND METHOD THEREOF

(75) Inventors: Kraig H. Allen, Leesburg, IN (US); Gary T. Dane, Bow, NH (US)

(73) Assignee: SYMMETRY MEDICAL MANUFACTURING, INC., Warsaw, IN (US)

( * ) Notice: Subject to any disclaimer, the term of this patent is extended or adjusted under 35 U.S.C. 154(b) by 922 days.

(21) Appl. No.: 13/228,957

(22) Filed: Sep. 9, 2011

(65) Prior Publication Data

US 2013/0061445 A1    Mar. 14, 2013

(51) Int. Cl.
*A61B 50/33* (2016.01)
*A61B 50/20* (2016.01)

(52) U.S. Cl.
CPC .............. *A61B 50/33* (2016.02); *A61B 50/20* (2016.02); *A61B 50/24* (2016.02); *Y10T 29/49826* (2015.01)

(58) Field of Classification Search
USPC .............. 29/428; 211/85.13, 70.1, 70.6, 124; 206/305, 306, 363, 364, 365, 366, 367, 206/368, 369, 370, 438, 562, 564, 565
See application file for complete search history.

(56) References Cited

U.S. PATENT DOCUMENTS

| | | | |
|---|---|---|---|
| 3,603,551 A * | 9/1971 | Peterson | 248/314 |
| 5,047,019 A * | 9/1991 | Sincock | 604/192 |
| 5,743,734 A * | 4/1998 | Heath et al. | 433/77 |
| 5,843,388 A | 12/1998 | Arroyo et al. | |
| 5,850,917 A * | 12/1998 | Denton et al. | 206/366 |
| 6,382,575 B1 * | 5/2002 | Frush et al. | 248/220.31 |
| 6,827,212 B2 | 12/2004 | Reaux | |
| 6,905,022 B2 | 6/2005 | Horrell | |
| 7,975,846 B2 | 7/2011 | Clegg et al. | |
| 8,075,849 B2 * | 12/2011 | Riley | 422/300 |
| 2004/0144739 A1 * | 7/2004 | Marek | 211/70.6 |
| 2008/0060958 A1 * | 3/2008 | Iske et al. | 206/366 |
| 2009/0146032 A1 | 6/2009 | Bettenhausen et al. | |

* cited by examiner

*Primary Examiner* — Christopher M Koehler
(74) *Attorney, Agent, or Firm* — Hayes Soloway, P.C.

(57) ABSTRACT

A medical instrument holder and method of holding a medical instrument is provided. The medical instrument holder includes a first substantially planar structure having at least a first aperture positioned therein. A second substantially planar structure is positioned approximately parallel to the first substantially planar structure. The second substantially planar structure has at least a second aperture positioned therein, wherein the second aperture is flexible. At least one holding structure is connected between the first substantially planar structure and the second substantially planar structure.

19 Claims, 9 Drawing Sheets

200

```
┌─────────────────────────────────────────────────────┐
│ A first substantially planar structure having at least a first │
│ aperture positioned approximately parallel to a second │
│ substantially planar structure with at least one holding structure, │──── 202
│ wherein the second substantially planar structure has at least a │
│ second aperture positioned therein, and wherein the second │
│ aperture is flexible │
└─────────────────────────────────────────────────────┘
                          │
┌─────────────────────────────────────────────────────┐
│ At least one medical instrument is placed within both the first │──── 204
│ aperture and the second aperture │
└─────────────────────────────────────────────────────┘
                          │
┌─────────────────────────────────────────────────────┐
│ A contact force is applied by the second apertures to a portion of │
│ the medical instrument proximately positioned within the second │──── 206
│ aperture │
└─────────────────────────────────────────────────────┘
```

MEDICAL INSTRUMENT HOLDER AND METHOD THEREOF

FIELD OF THE DISCLOSURE

The present disclosure is generally related to holding devices and more particularly is related to a medical instrument holder.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Additionally, medical instruments must be sterilized properly to ensure that bacteria and contaminants are not transferred between patients. Many conventional sterilization containers used today often harbor bacteria within crevices, cracks, or other small areas of the container. The bacteria may build up in these areas over time, resulting in a non-sterilized container which is prone to contaminating medical instruments contained therein. Many of these medical sterilization containers do not allow for their various components to be separated for a thorough cleaning, but medical technicians remove them anyways, which may cause damage to the sterilization container. This damage may lead to an inoperable or ineffective sterilization container.

Thus, a heretofore unaddressed need exists in the industry to address the aforementioned deficiencies and inadequacies.

SUMMARY OF THE DISCLOSURE

Embodiments of the present disclosure provide a system and method for a medical instrument holder. Briefly described, in architecture, one embodiment of the system, among others, can be implemented as follows. A medical instrument holder includes a first substantially planar structure having at least a first aperture positioned therein. A second substantially planar structure is positioned approximately parallel to the first substantially planar structure. The second substantially planar structure has at least a second aperture positioned therein, wherein the second aperture is flexible. At least one holding structure is connected between the first substantially planar structure and the second substantially planar structure.

The present disclosure can also be viewed as providing methods of holding a medical instrument holder. In this regard, one embodiment of such a method, among others, can be broadly summarized by the following steps: positioning a first substantially planar structure having at least a first aperture positioned approximately parallel to a second substantially planar structure with at least one holding structure, wherein the second substantially planar structure has at least a second aperture positioned therein, and wherein the second aperture is flexible; placing at least one medical instrument within both the first aperture and the second aperture; and applying a contact force by the second apertures to a portion of the medical instrument proximately positioned within the second aperture.

In another embodiment, the present disclosure can also be viewed as a medical instrument holder. Briefly described, in architecture, one embodiment of the system, among others, can be implemented as follows. A first rigid structure has at least one substantially planar portion having a plurality of first aperture positioned therein. The at least one substantially planar portion is affixed to at least two sidewalls, each positioned perpendicular to the at least one substantially planar portion. A flexible substantially planar membrane is positioned approximately parallel to the first substantially planar structure and interior of the at least two sidewalls, wherein the flexible substantially planar membrane includes a plurality of second apertures positioned therein and a plurality of third apertures positioned therein. At least two substantially rigid posts connected to the at least one substantially planar portion at a first side, wherein a second side of each of the at least two substantially rigid posts is removably engaged to one of the plurality of third apertures. At least one medical instrument is removably positioned within at least one of the plurality of first apertures and at least one of the plurality of second apertures. A contact force is applied by the at least one of the plurality of second apertures to a portion of the medical instrument proximately positioned within the at least one of the plurality of second aperture.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 9 is a flowchart illustrating a method of constructing a medical instrument holder, in accordance with the first exemplary embodiment of the disclosure.

DETAILED DESCRIPTION

Figure 1:
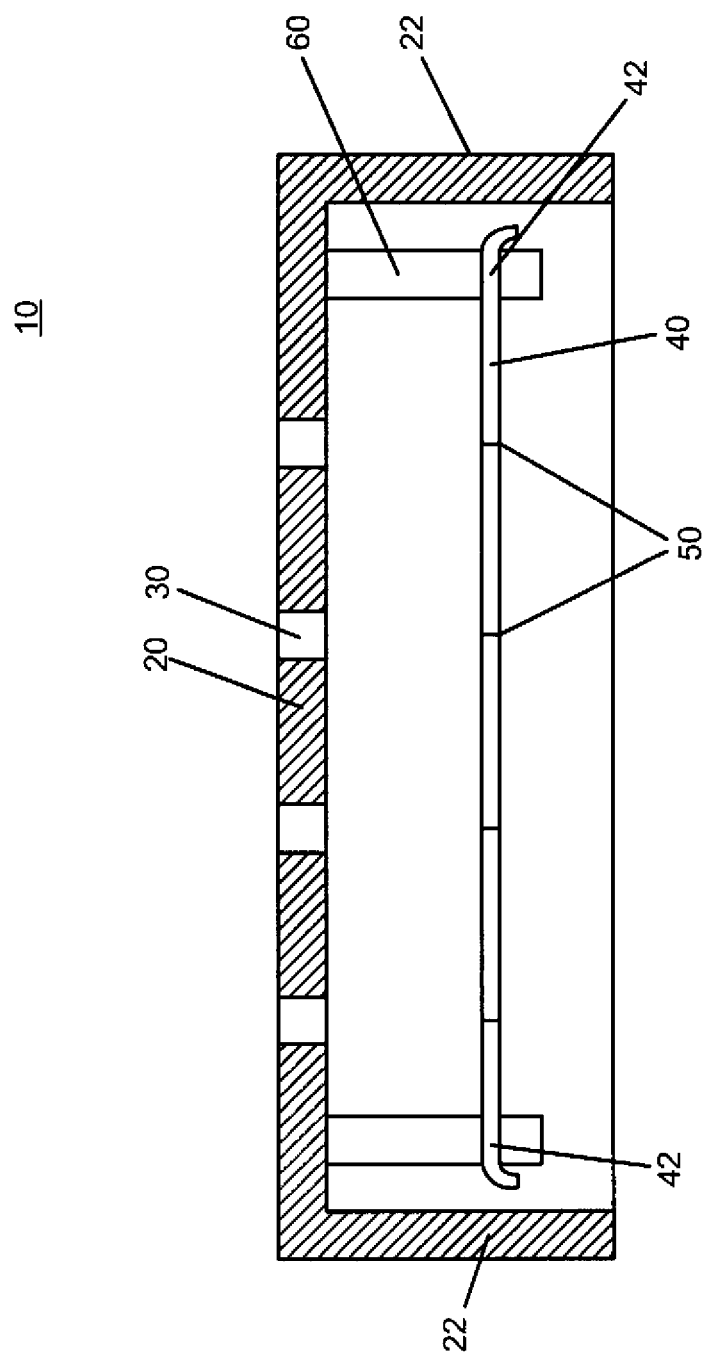
FIG. 1 is a cross-sectional illustration of a medical instrument holder, in accordance with a first exemplary embodiment of the present disclosure.

FIG. 1 is a cross-sectional illustration of a medical instrument holder 10, in accordance with a first exemplary embodiment of the present disclosure. The medical instrument holder 10, which may be referred to herein simply as 'holder 10,' includes a first substantially planar structure 20 having at least a first aperture 30 positioned therein. A second substantially planar structure 40 is positioned approximately parallel to the first substantially planar structure 20. The second substantially planar structure 40 has at least a second aperture 50 positioned therein, wherein the second aperture 50 is flexible. At least one holding structure 60 is connected between the first substantially planar structure 20 and the second substantially planar structure 40.

The holder 10 may be used within any industry utilizing medical tools, such as tools, instruments, or any other type of implement used for surgical procedures, operations, or other medical procedures. For example, the holder 10 may be used in surgical environments to hold medical instruments before, during and/or after a surgical procedure, or a medical instrument sterilization process. Similarly, the holder 10 may be used with dental instruments for dental operations, routine cleanings, or for any other use. Other settings and uses within the medical field are also envisioned, all of which are considered within the scope of the present disclosure. Although the holder 10 may be used in a variety of ways to hold a variety of medical instruments, it may be particularly useful with holding or retaining medical instruments with small shafts. For example, many dental instruments have handles or shafts with relatively small diameters or widths, which may be challenging to retain with conventional systems.

The first substantially planar structure 20 may be any size length, width, or thickness, but is preferably sized such that it can conveniently be used with existing medical instrument sterilization environments, such as autoclaves, or with existing trays, tables, or other similar structures. The first substantially planar structure 20 may be substantially rigid, such that it is able to retain its planar shape. However, the first substantially planar structure 20 may also be fully or partially flexible, such as when it is constructed from a flexible membrane material.

The first substantially planar structure 20 may be integrally included with any number of sidewalls 22. For example, the first substantially planar structure 20 may be integral with a medical instrument tray having a plurality of sidewalls 22 on two, three, or four sides of the first substantially planar structure 20. The sidewalls 22 may be positioned perpendicular to the first or substantially perpendicular to the first substantially planar structure 20. Of course, other designs for the sidewalls 22 exist, all of which are included within the scope of the present disclosure.

The first substantially planar structure 20 may also include any number or type of locking devices, fasteners, identification elements, or other components that are known within the art. Additionally, the first substantially planar structure 20 may be a portion of another structure, such as a portion of a structure having a plurality of sidewalls.

The first aperture 30 is positioned within the first substantially planar structure 20. The at least one first aperture 30 may include any number of first apertures 30, such as 10, 20, 30, or more first apertures 30, each of which may have any size diameter or width, and may be positioned in any location of the first substantially planar structure 20. Commonly, the plurality of first apertures 30 may be arranged in a grid, wherein the various sized first apertures 30 are positioned in a convenient manner, such as in an ascending or descending order by size. When the first substantially planar structure 20 is constructed from a substantially rigid material, the first aperture 30 may have a diameter or width that is larger than the outer diameter or width of a shaft or handle of a medical instrument. This may allow the medical instrument to be successfully positioned within the first aperture 30 without forcibly contacting all sides of the first aperture 30.

For example, the first aperture 30 may be purposely sized larger than a medical instrument positioned therein, which allows the medical instrument to be inserted and removed from the first aperture 30 with ease. Since medical instruments may include a variety of different sizes, the plurality of first apertures 30 may be sized to include some first apertures 30 with a first size and some of the first apertures 30 with a second size, wherein the first size is different from the second size (see also FIG. 8). If the first substantially planar structure 20 is constructed from a fully or partially flexible material, the size of the first aperture 30 may vary. For example, the first aperture 30 may be flexible such that it enlarges to accommodate the shaft of a medical instrument, similar to the second aperture 50 of the second substantially planar structure 40.

The second substantially planar structure 40 may also be any size width, length or thickness, and may be sized to substantially match the size of the first substantially planar structure 20. The second substantially planar structure 40 may be constructed from a substantially flexible or pliable material, such as silicon, which is capable of being retained with the holding structures 60, such that is has a substantially planar shape. Of course, when the second substantially planar structure 40 is not being retained with the holding structure 60, it may have a non-planar shape. The second substantially planar structure 40 may be constructed with materials that can withstand a medical sterilization environment, which often has high temperatures, wet environments, contact with chemicals, or other sterilizing materials.

The position of the second substantially planar structure 40 is approximately parallel to the first substantially planar structure 20. This may be characterized as any position that allows a portion of the planar surface of the second substantially planar structure 40 to be substantially near a first aperture 30 of the first substantially planar structure 20. For example, approximately parallel may include a parallel configuration to a certain degree, such as within 1°, 5°, 10°, and/or 30°, etc., or any other position. Commonly, the second substantially planar structure 40 is placed approximately parallel to the first substantially planar structure 20 by a staff member or other medical technician, so its position with respect to the first substantially planar structure 20 may not be precise or exact.

The second aperture 50 positioned within the second substantially planar structure 40 may commonly include a plurality of second apertures 50. For example, it may be common for the second substantially planar structure 40 to include 10, 20, or 50, or more second apertures 50 positioned therein. The second aperture 50 may be positioned in any location of the second substantially planar structure 40, such as oriented in a grid, a specific pattern, or positioned in relation to the first aperture 30 of the first substantially planar structure 20. The second aperture 50 is flexible, meaning that it is able to conform around the shaft or handle of a medical instrument that is positioned therein.

Figure 5:
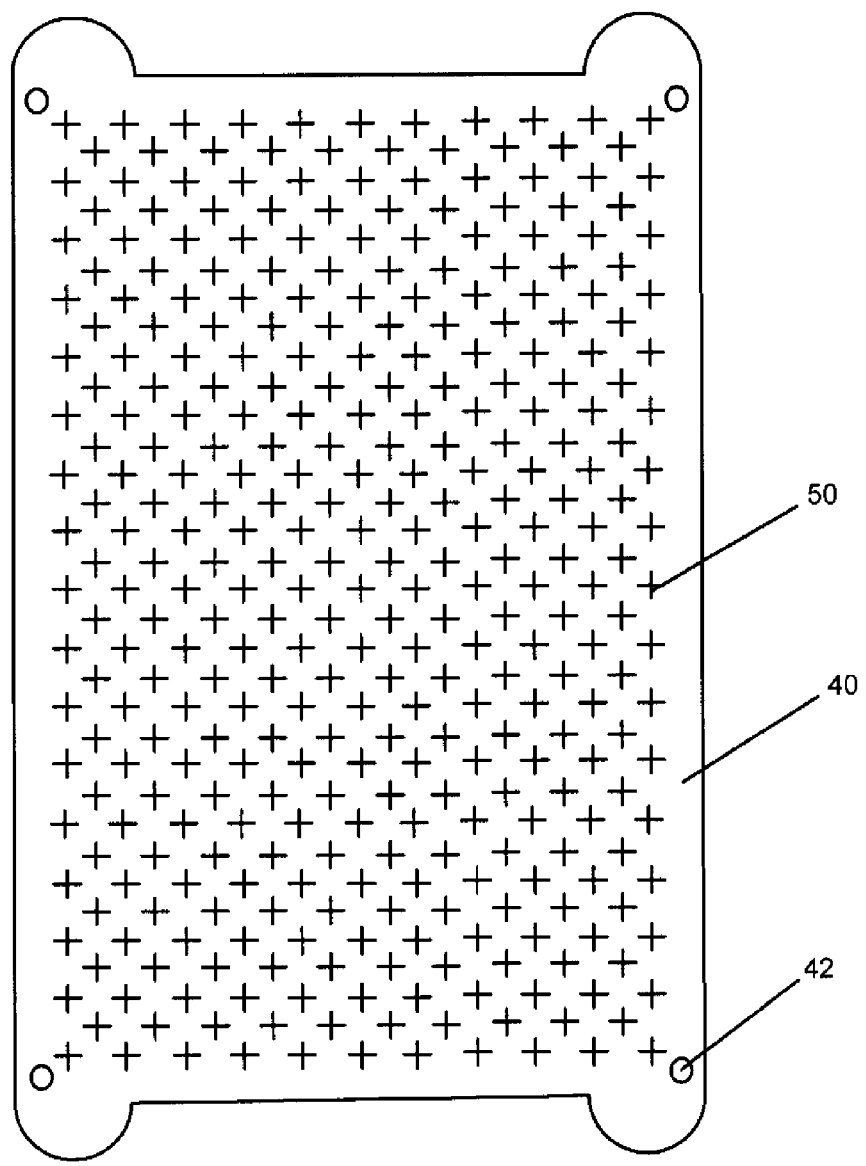
FIGS. 5-7 are top view illustrations of the second substantially planar structure of the medical instrument holder, in accordance with the first exemplary embodiment of the present disclosure.
Figure 6:
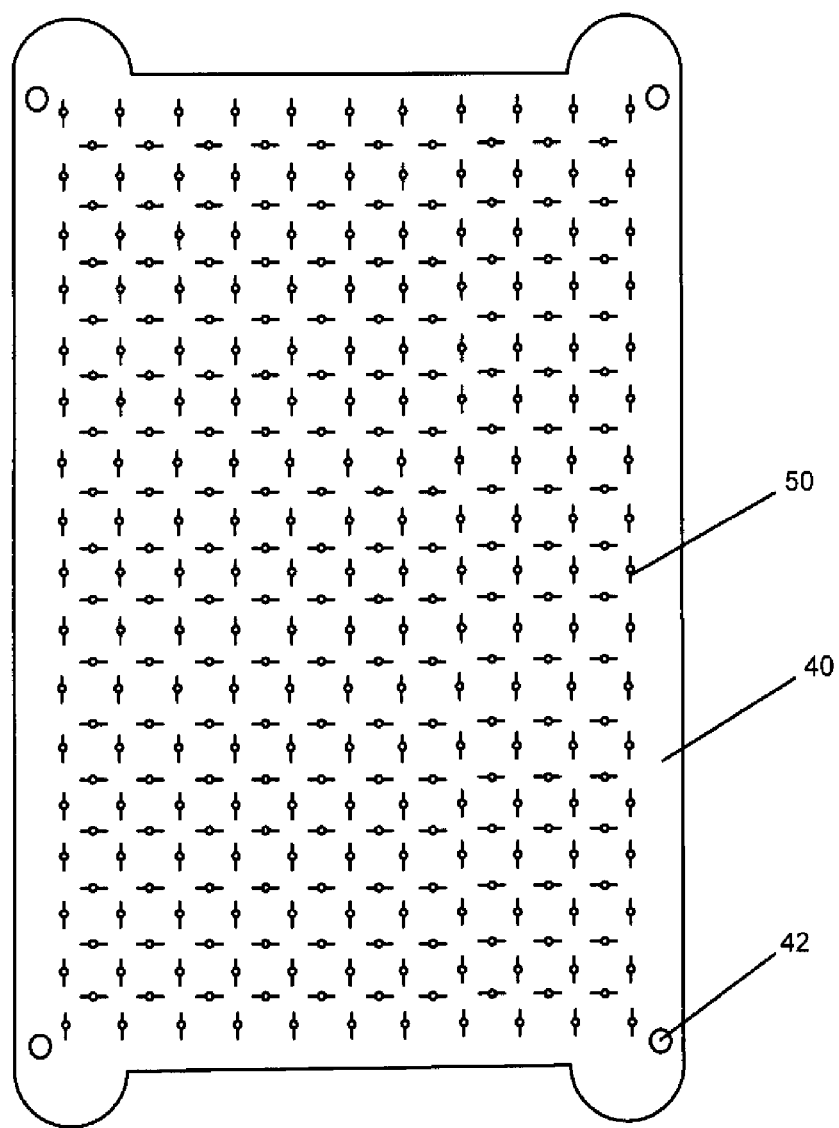
Figure 7:
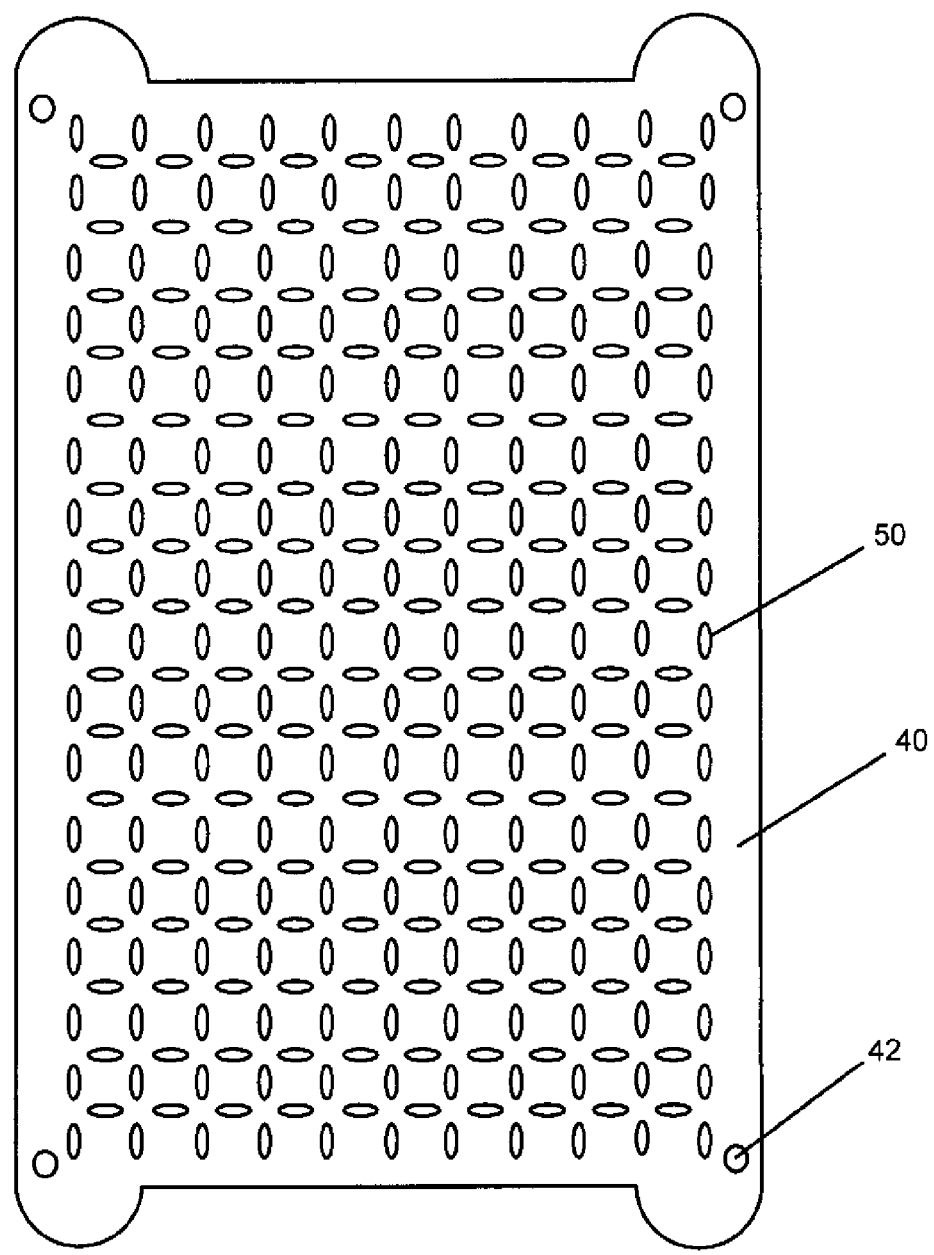

For example, the second aperture 50 may be sized smaller than the cross-sectional dimension of the shaft of the medical instrument, and enlargeable to allow the shaft to be positioned therein. This allows the second aperture 50 to apply a contact force on the portion of the medical instrument that is positioned within the second aperture 50. In accordance with this disclosure, the contact force may be a force applied to a medical instrument by the second aperture 50, which is sufficient to substantially secure the medical instrument in a stationary position with respect to the second substantially planar structure 40. The second aperture 50 may include a variety of designs, including a design with a slot having material that is capable of being biased by the shaft of the medical instrument, which acts to retain the medical instrument. FIGS. 5-7 provide more description of the variations of the second aperture 50.

The at least one holding structure 60 may include any number of holding structures 60 that are positioned between the first substantially planar structure 20 and the second substantially planar structure 40. For example, as is shown in FIG. 1, the holding structure 60 may include a rigid post that is affixed to the first substantially planar structure 20 at one end and allows the second substantially planar structure 40 to be attached to another end thereof. Accordingly, the second substantially planar structure 40 may have receiving structures 42 to engage with the holding structure 60, such as holes or fasteners. The holding structure 60 may also include any other structures that are affixed to the sidewalls 22 of the first substantially planar structure 20. The holding structures 60 may dictate the distance between the first substantially planar structure 20 and the second substantially planar structure 40. Any distance may be acceptable, as may be dependent on the intended use of the holder 10 or the medical instruments that it is used with. For example, the distance between the first and second substantially planar structures 20, 40 may be a centimeter, a few centimeters, or 10 or more centimeters.

In use, the holding structure 10 may conveniently hold a number of medical instruments, providing organized and reliable access to any of the medical instruments. When the medical instruments are positioned within the first and second apertures 30, 50, they will be partially located between the first and second substantially planar structures 20, 40. A portion of the medical instrument may be positioned on an exterior side, i.e., the side facing away from the first substantially planar structure 20, of the second substantially planar structure 40. As is shown in FIG. 1, any sidewalls 22, or any portion of sidewalls 22 of the first substantially planar structure 20 may be sized to act as a base or footing for the holder 10. This may prevent medical instruments from contacting the surface of a table or other holding unit.

Figure 2:
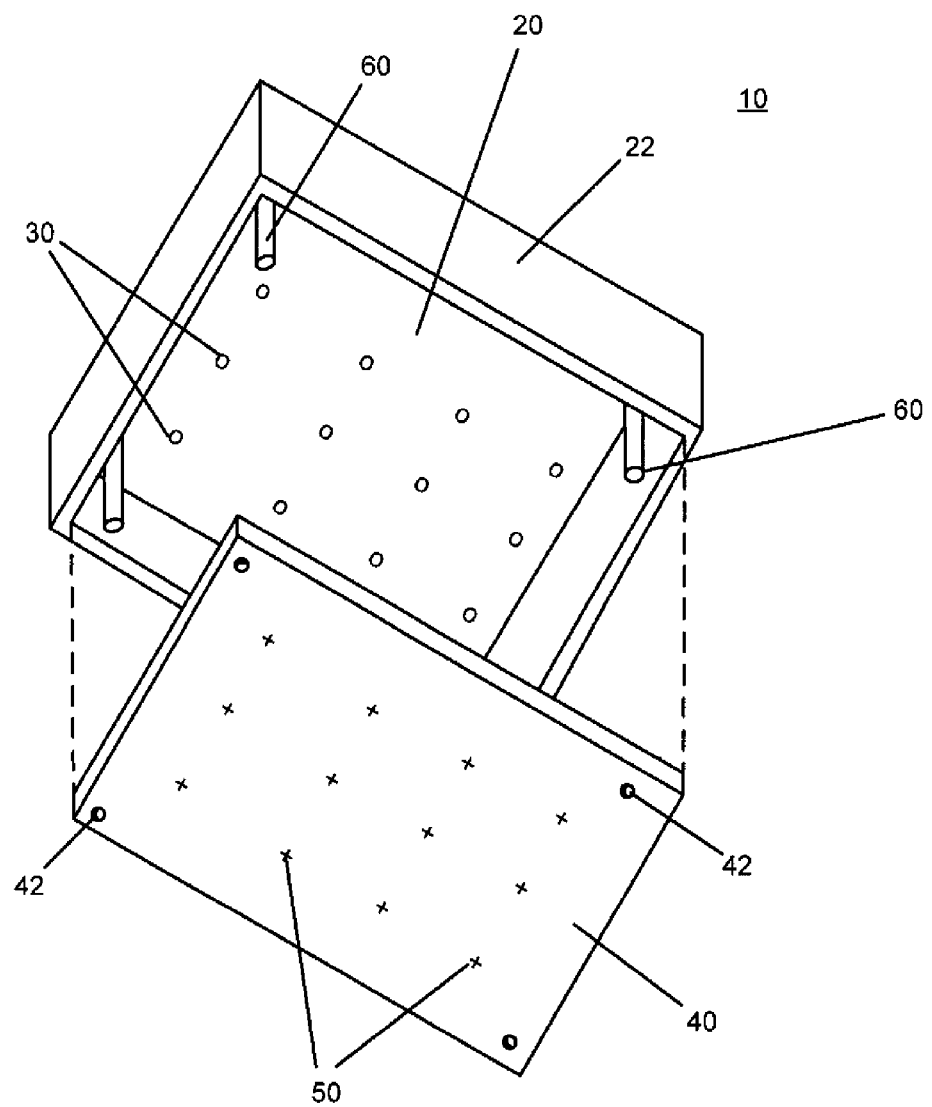
FIG. 2 is an exploded plan view illustration of the medical instrument holder, in accordance with the first exemplary embodiment of the present disclosure.

FIG. 2 is an exploded plan view illustration of the medical instrument holder 10, in accordance with the first exemplary embodiment of the present disclosure. The exploded view of FIG. 2 illustrates a non-engaged configuration between the first and second substantially planar structures 20, 40. The broken lines illustrate the intended path of the second substantially planar structure 40 as it is moved to an engaged configuration with the first substantially planar structure 20. As can be seen, the holding structures 60 of the first substantially planar structure 20 may be designed to conveniently engage with the receiving structures 42 of the second substantially planar structure 40. Also, it can be seen that the first apertures 30 may be positioned to substantially line up with the second apertures 50 of the second substantially planar structure 40. However, it is noted that the placement of the first and second apertures 30, 50 does not necessarily need to be based on lining up the first and second apertures 30, 50, since the number of first or second apertures 30, 50 may be numerous enough to allow for many instrument positions in the holder 10.

Figure 3:
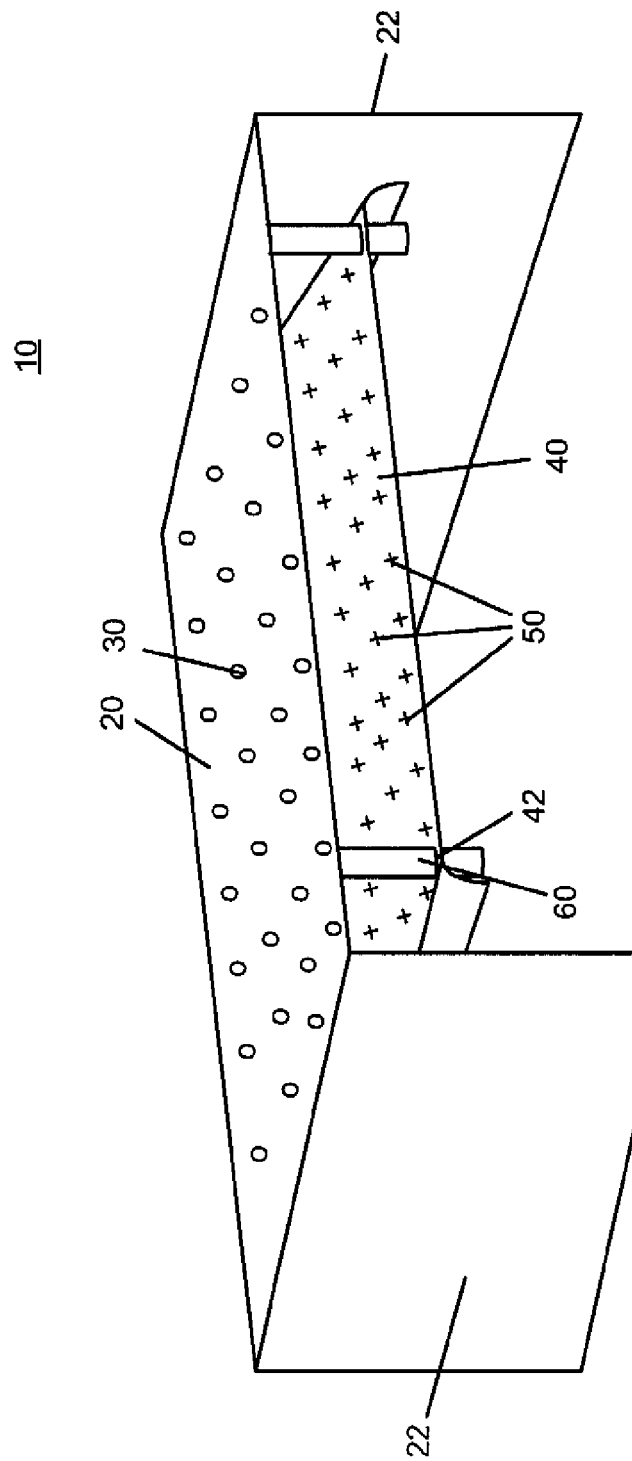
FIG. 3 is a plan view illustration of the medical instrument holder, in accordance with the first exemplary embodiment of the present disclosure.

FIG. 3 is a plan view illustration of the medical instrument holder 10, in accordance with the first exemplary embodiment of the present disclosure. As can be seen, the second substantially planar structure 40 is shown engaged with the holding structures 60, thereby holding the second substantially planar structure 40 proximate to the first substantially planar structure 20. In this position, the center portion of the second substantially planar structure 40 (the portion of the second substantially planar structure 40 that is located between the holding structures 60) may be retained tightly between the holding structures 60, thereby providing the planar shape of the second substantially planar structure 40. As shown, the ends of the second substantially planar structure 40 may droop down, since they are not retained between the holding structures 60.

It can be seen in FIG. 3 that the first apertures 30 of the first substantially planar structure 20 may be proximate to the second apertures 50 of the second substantially planar structure 40. This allows a medical instrument to be positioned within both the first aperture 30 and the second aperture 50. It can also be seen in FIG. 3 that the sidewalls 22 may act as legs for the holder 10, thereby allowing the first and second substantially planar structures 20, 40 to be retained off the ground or table surface. This may prevent any medical instrument inserted within the first and second apertures 30, 50 from contacting the ground or table surface.

Figure 4:
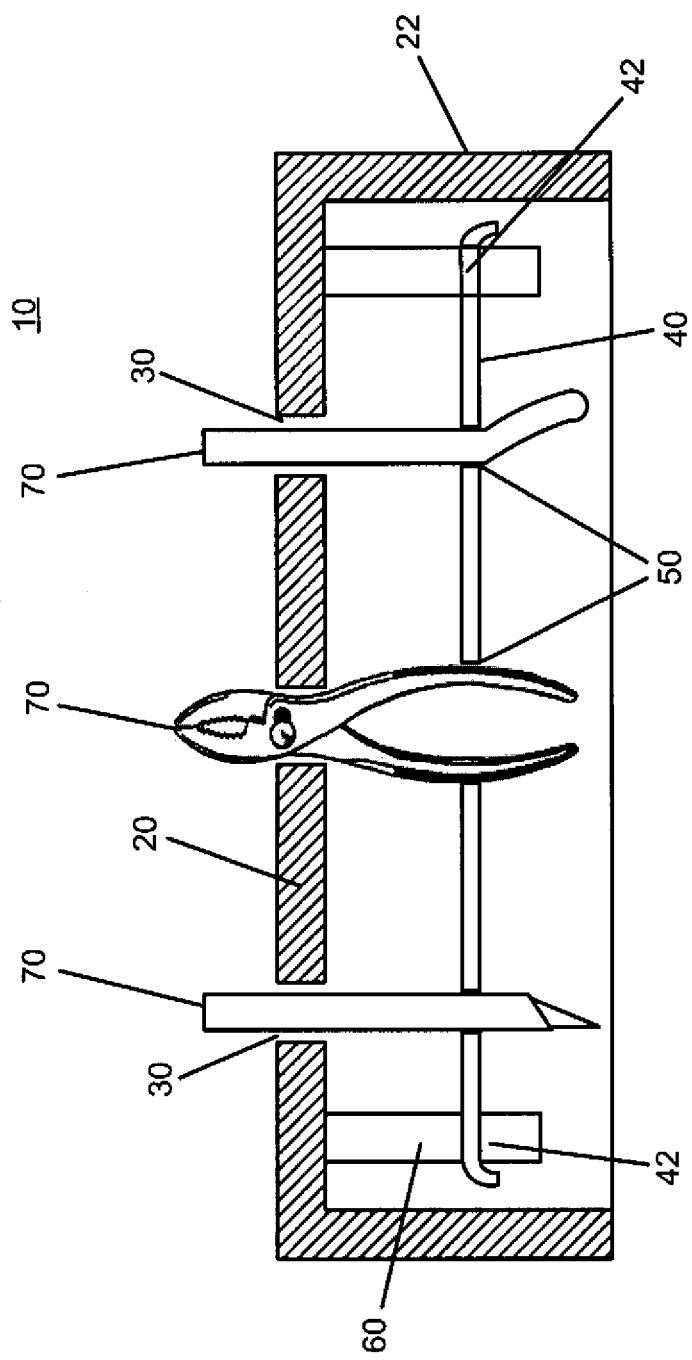
FIG. 4 is a cross-sectional illustration of the medical instrument holder in use, in accordance with the first exemplary embodiment of the present disclosure.

FIG. 4 is a cross-sectional illustration of the medical instrument holder 10 in use, in accordance with the first exemplary embodiment of the present disclosure. Specifically, FIG. 4 shows the medical instrument holder 10 in use with a plurality of medical instruments 70. The medical instruments 70, which may include any type or variety of medical instrument 70 or other medical tool, may be positioned within the first aperture 30 of the first substantially planar structure 20. The first apertures 30 may be sized to provide a large tolerance around the cross section of the medical instrument 70, which may allow the first aperture 30 to support the medical instrument 70 radially, but not support the medical instrument 70 along an elongated axis of the medical instrument 70.

The medical instrument 70 may be positioned within the second aperture 50 as well, which allows the medical instrument 70 to be retained within both the first and second apertures 30, 50. This is accomplished through the contact force applied by the second aperture 50 to the portion of the medical instrument 70 that is positioned within the second aperture 50. This contact force may be created from the flexibility or elasticity of the second aperture 50, or the structure of the second substantially planar structure 40 surrounding the second aperture 50. This contact force may be sufficient enough to retain the medical instrument 70 in all directions, but may also allow the medical instrument 70 to be removed with a strong enough axial force (along the axis of the medical instrument 70). Thus, as can be seen, a medical instrument 70 within this position in the medical instrument holder 10 may be sufficiently retained during a sterilization process, during transportation, or at any other time.

FIGS. 5-7 are top view illustrations of the second substantially planar structure 40 of the medical instrument holder 10, in accordance with the first exemplary embodiment of the present disclosure. Each of the second substantially planar structures 40 illustrated in FIGS. 5-7 depict a variation of the second aperture 50. For example, FIG. 5 depicts the second aperture 50 as a bisecting slot with a crosshatched structure within the second substantially planar structure 40, which also has the receiving structures 42. The bisecting slot may be formed by cutting two slots through the second substantially planar structure 40. When a medical tool is inserted into the bisecting slot, the tool shaft may bias the material of the second substantially planar structure 40 immediately proximate to the bisecting slot. That material may then push against the shaft of the medical instrument to retain it in a position within the bisecting slot. Also shown in FIG. 5 is the numerous quantity of second apertures 50 positioned along a grid. This may allow for insertion of a medical instrument into the holder 10 in many different ways, thereby providing efficient use of the holder 10.

In FIG. 6, the second substantially planar structure 40 has the receiving structures 42 and a plurality of second apertures 50 depicted as slots with holes. The slot with hole structure may allow for the shaft of a medical instrument to be inserted into the hole portion of the second aperture 50. The slot positioned on either side of the hole may allow the hole to flex or enlarge to accommodate the shaft. In FIG. 7, the second substantially planar structure 40 has the receiving structures 42 and a plurality of second apertures 50 depicted as full holes. The full hole design may include holes that have any shape, such as elliptically shaped structure as is shown, or circular shapes, etc. The full hole may not include a slot, but may still flex or enlarge around the shaft of a medical instrument when it is inserted into the second aperture 50. Any of the designs of the second aperture 50 in FIGS. 5-7 may be used, alone or in combination with each other, all of which are considered within the scope of the present disclosure. Additionally, other variations of the second aperture 50 are within the scope of this disclosure.

Figure 8:
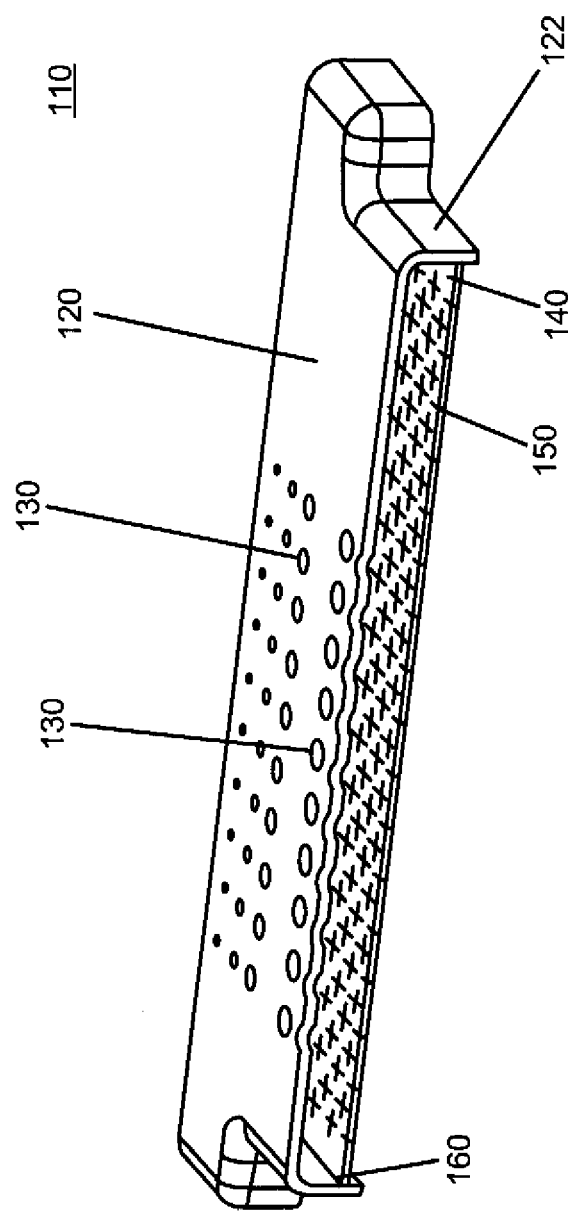
FIG. 8 is a plan view illustration of the medical instrument holder, in accordance with a second exemplary embodiment of the present disclosure.

FIG. 8 is a plan view illustration of the medical instrument holder 110, in accordance with a second exemplary embodiment of the present disclosure. The medical instrument holder 110, which may be referred to as 'holder 110,' may include any of the features, components or functions of the holder 10 of the first exemplary embodiment. As can be seen, the holder 110 includes a first substantially planar structure 120 with a sidewall 122, the first substantially planar structure 120 having at least a first aperture 130 positioned therein. A second substantially planar structure 140 is positioned approximately parallel to the first substantially planar structure 120. The second substantially planar structure 140 has at least a second aperture 150 positioned therein, wherein the second aperture 150 is flexible.

Different from the first exemplary embodiment, the holder 110 includes a holding structure 160 that is integral with the sidewall 122 of the first substantially planar structure 120. The integral holding structure 160 may include any type of holding device, such as a fastener, or an integral connection. This may be a removable connection, a permanent connection or any combination thereof. As can be seen, the holding structure 160 connects the first substantially planar structure 120 to the second substantially planar structure 140. Also shown in FIG. 8 are the first apertures 130 having a variety of different sizes, which may accommodate medical instruments with varying sized shafts. The first apertures 130 may or may not be lined up with the second apertures 150 of the second substantially planar structure 140.

FIG. 9 is a flowchart 200 illustrating a method of holding a medical instrument, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, a first substantially planar structure having at least a first aperture positioned approximately parallel to a second substantially planar structure with at least one holding structure, wherein the second substantially planar structure has at least a second aperture positioned therein, and wherein the second aperture is flexible. At least one medical instrument is placed within both the first aperture and the second aperture (block 204). A contact force is applied by the second apertures to a portion of the medical instrument proximately positioned within the second aperture (block 206). The method may also include any functions or be operable with any features, structures, or other aspects described herein with respect to FIGS. 1-8.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A medical instrument holder comprising:
   a first substantially planar structure having at least a first aperture positioned therein;
   a second substantially planar structure positioned approximately parallel to the first substantially planar structure, the second substantially planar structure having at least a second aperture positioned therein, wherein the second substantially planar structure is flexible;
   a plurality of third apertures positioned within the second substantially planar structure; and
   a plurality of holding structures extending from the first substantially planar structure, wherein at least a portion of the plurality of holding structures engage with at least a portion of the plurality of third apertures within the second substantially planar structure, and wherein the second substantially planar structure is stretched between the portion of the plurality of holding structures.

2. The medical instrument holder of claim 1, further comprising a plurality of sidewalls integrally connected with the first substantially planar structure, wherein the plurality of sidewalls are each positioned approximately perpendicularly to the first substantially planar structure.

3. The medical instrument holder of claim 1, further comprising a plurality of first apertures positioned in the first substantially planar structure and a plurality of second apertures within the second substantially planar structure.

4. The medical instrument holder of claim 3, wherein the plurality of first apertures positioned within the first substantially planar structure include at least a first aperture size and a second aperture size, wherein the first aperture size is different from the second aperture size.

5. The medical instrument holder of claim 1, wherein the second aperture positioned within the second substantially planar structure is enlargeable between at least a first position where the second aperture is smaller than a cross-section of a medical instrument and a second position where the second aperture is larger than the cross-section of the medical instrument.

6. The medical instrument holder of claim 5, wherein the second position of the second aperture is sized to provide a contact force on a portion of the medical instrument positioned substantially within the second aperture.

7. The medical instrument holder of claim 1, wherein the second aperture further comprises a bisecting slot with crosshatched structure.

8. The medical instrument holder of claim 1, wherein the second aperture further comprises a slot with hole structure.

9. The medical instrument holder of claim 1, wherein the second aperture further comprises an elliptically shaped hole.

10. The medical instrument holder of claim 1, wherein the at least one holding structure connected between the first substantially planar structure and the second substantially planar structure is connected to at least two sidewalls integral with the first substantially planar structure.

11. The medical instrument holder of claim 1, wherein the at least one holding structure further comprises a rigid post attached to the first substantially planar structure at a first end.

12. The medical instrument holder of claim 1, wherein the second substantially planar structure further comprises a first planar side and a second planar side, wherein the first planar side opposes the second planar side, wherein the first planar side is positioned between the first substantially planar structure and the second planar side, and wherein the second planar side is free from contact.

13. A medical instrument holder comprising:
a first rigid structure having at least one substantially planar portion having a plurality of first apertures positioned therein, wherein the at least one substantially planar portion is affixed to at least two sidewalls, each positioned perpendicular to the at least one substantially planar portion;
a flexible substantially planar membrane positioned approximately parallel to the first substantially planar structure and interior of the at least two sidewalls, wherein the flexible substantially planar membrane includes a plurality of second apertures positioned therein and a plurality of third apertures positioned therein;
at least two substantially rigid posts connected to the at least one substantially planar portion at a first side, wherein a second side of each of the at least two substantially rigid posts is removably engaged to one of the plurality of third apertures; and
at least one medical instrument removably positioned within at least one of the plurality of first apertures and at least one of the plurality of second apertures, wherein a contact force is applied by the at least one of the plurality of second apertures to a portion of the medical instrument proximately positioned within the at least one of the plurality of second aperture.

14. A method for holding a medical instrument, the method comprising the steps of:
positioning a first substantially planar structure having at least a first aperture positioned approximately parallel to a second substantially planar structure with at least one holding structure, wherein the second substantially planar structure is flexible and has at least a second aperture positioned therein, and wherein the second aperture is flexible, wherein the second substantially planar structure is stretched between the at least one holding structure which is engaged with at least one third aperture positioned of the second substantially planar structure;
placing at least one medical instrument within both the first aperture and the second aperture; and
applying a contact force by the second apertures to a portion of the medical instrument proximately positioned within the second aperture.

15. The method of claim 14, further comprising the step of constructing the second substantially planar structure from a flexible membrane integrally having a plurality of second apertures positioned therein.

16. The method of claim 15, further comprising the step of constructing the plurality of second apertures with a bisecting slot with crosshatched structure.

17. The method of claim 15, further comprising the step of constructing the plurality of second apertures with a slot with hole structure.

18. The method of claim 15, further comprising the step of constructing the plurality of second apertures with an elliptically shaped hole structure.

19. The method of claim 14, further comprising the steps of: providing a plurality of first apertures within the first substantially planar structure; and sizing the plurality of first apertures to include at least a first aperture size and a second aperture size, the second aperture size different from the first aperture size.

* * * * *